(12) United States Patent
Mocanu et al.

(10) Patent No.: US 8,906,076 B2
(45) Date of Patent: *Dec. 9, 2014

(54) ANGULATED LOCKING PLATE AND SCREW

(71) Applicant: OsteoMed LLC, Addison, TX (US)

(72) Inventors: Viorel Mocanu, Lewisville, TX (US); Joel Bales, Carrollton, TX (US)

(73) Assignee: OsteoMed LLC, Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/046,678

(22) Filed: Oct. 4, 2013

(65) Prior Publication Data

US 2014/0039563 A1    Feb. 6, 2014

Related U.S. Application Data

(63) Continuation-in-part of application No. 12/535,816, filed on Aug. 5, 2009, now Pat. No. 8,597,334.

(60) Provisional application No. 61/106,511, filed on Oct. 17, 2008.

(51) Int. Cl.
*A61B 17/80* (2006.01)
*A61B 17/86* (2006.01)

(52) U.S. Cl.
CPC ......... *A61B 17/8057* (2013.01); *A61B 17/8625* (2013.01)
USPC ....................................................... 606/291

(58) Field of Classification Search
USPC ................... 606/70, 71, 280–299, 300–331
See application file for complete search history.

(56) References Cited

U.S. PATENT DOCUMENTS

| | | | |
|---|---|---|---|
| 6,129,730 A * | 10/2000 | Bono et al. ............ | 606/291 |
| 6,322,562 B1 | 11/2001 | Wolter | |
| 6,440,135 B2 | 8/2002 | Orbay et al. | |
| 6,730,091 B1 | 5/2004 | Pfefferle et al. | |
| 7,128,744 B2 | 10/2006 | Weaver et al. | |
| 7,172,593 B2 | 2/2007 | Trieu et al. | |
| 7,250,053 B2 | 7/2007 | Orbay | |
| 7,717,945 B2 | 5/2010 | Jensen et al. | |
| 7,776,076 B2 | 8/2010 | Grady, Jr. et al. | |
| 7,887,570 B2 | 2/2011 | Ziolo et al. | |
| 7,976,570 B2 | 7/2011 | Wagner et al. | |

(Continued)

FOREIGN PATENT DOCUMENTS

| | | |
|---|---|---|
| WO | WO 00/86012 A1 | 11/2000 |
| WO | WO-2005/018472 A1 | 3/2005 |
| WO | WO-2005/055842 A1 | 6/2005 |

OTHER PUBLICATIONS

Notification of Transmittal of the International Search Report and the Written Opinion of the International Searching Authority, or the Declaration; International Application No. PT/US2009/060860; International Filing Date Oct. 15, 2009.

(Continued)

*Primary Examiner* — Christopher Beccia
(74) *Attorney, Agent, or Firm* — Fulbright & Jaworkski LLP (57) ABSTRACT

An improved fixation plate using at least a double helix screw as disclosed. The double helix screw may include alternate embodiments comprising three, four, or more threads. The helix thread screw intertwines with double helix thread in the screw hole of the fixation plate providing enhanced fixation to a fractured bone.

17 Claims, 7 Drawing Sheets

(56) References Cited

U.S. PATENT DOCUMENTS

| | | | |
|---|---|---|---|
| 8,597,334 B2 * | 12/2013 | Mocanu | 606/281 |
| 2002/0058940 A1 | 5/2002 | Frigg et al. | |
| 2004/0059335 A1 | 3/2004 | Weaver et al. | |
| 2004/0181228 A1 | 9/2004 | Wagner et al. | |
| 2005/0261688 A1 | 11/2005 | Grady, Jr. et al. | |
| 2007/0088360 A1 | 4/2007 | Orbay et al. | |
| 2008/0234752 A1 | 9/2008 | Dahners | |
| 2009/0318979 A1 | 12/2009 | Raines et al. | |

OTHER PUBLICATIONS http://www.stratmed.co.za/viper.htm, last accessed Jun. 25, 2007, pp. 1-3.

Kinetikos Medical Inc., Surgical Technique, Viper With VALT, Distal Radius Plate with Variable Angle Locking Technology; KMI brochure 2006, pp. 1-8.

* cited by examiner

ANGULATED LOCKING PLATE AND SCREW

CROSS-REFERENCE TO RELATED APPLICATIONS

This application claims the benefit of U.S. patent application Ser. No. 12/535,816 titled "Angulated Locking Screw/Plate Interface" and filed Aug. 5, 2009, which depends on provisional patent application No. 61/106,511 titled "Angulated Locking Screw/Plate Interface" and filed Oct. 17, 2008, which are both incorporated herein by reference.

FIELD OF THE INVENTION

The present disclosure relates generally to repairing bone fractures, and more particularly, to an angulated locking plate/screw interface.

BACKGROUND OF THE INVENTION

When repairing a broken, fractured, or shattered bone, a physician may often be faced with the task of affixing a fixation plate to the bone in order to align the bone, and possibly, to hold bone fragments together. In order to affix the fixation plate to the bone, a surgeon may insert a locking bone screw through one of a plurality of threaded screw holes in the fixation plate and into a predrilled hole in the bone. Alternatively, self-drilling screws may be used. Since numerous threaded screw holes may be spread out across the entirety of the fixation plate, the surgeon may affix virtually any portion of the fixation plate to the bone by inserting a suitable number of locking bone screws through the plate and into the bone.

The trend in fixation for many medical practice areas such as the small bone orthopedic market and the craniofacial market is to use locking screws and plates that prevent the locking bone screws from backing out of the fixation plate once inserted. To achieve this lockable engagement, the inner surface of each threaded screw hole may be threaded to engage a corresponding set of locking threads on the head of each locking bone screw. Consequently, as a locking bone screw is screwed into one of the threaded screw holes in the fixation plate, the locking threads in the screw hole and the locking threads on the head of the locking bone screw may deform against each other to lock the locking bone screw into the fixation plate.

In certain cases, proper placement and positioning of the fixation plate may call for inserting a locking screw into a threaded screw hole at an angle other than perpendicular to the central axis of the threaded screw hole. For example, if the underlying bone beneath a particular screw hole is weak due to its proximity to a fracture line, the surgeon may wish to angle the bone screw away from the fracture line so as to anchor the screw into a more solid bony mass. Consequently, the ability to lockably engage a bone screw into a fixation plate at an angle off of perpendicular from the plate maybe a desirable feature for a surgeon repairing a broken, fractured, or shattered bone.

SUMMARY OF THE INVENTION

The present disclosure provides for a system and method for lockably engaging bone screws into a fixation plate. In particular embodiments, the system may include a locking fixation plate including a threaded screw hole defined by an inner surface surrounding the threaded screw hole. The inner surface may include an upper countersink and a threaded portion, and the threaded portion may include a pair of threads arranged in a double helix configuration. In particular embodiments, the system may further include a screw comprising a generally conical head tapering into a generally cylindrical shaft that ends at a tip and double helix threads beginning near the tip and extending along the generally cylindrical shaft and onto the generally conical head. In particular embodiments, a thread height of each of the double helix threads may be constant over a majority of the generally cylindrical shaft and taper as the threads extend onto the head.

In particular embodiments, the portion of the said threads disposed on the generally conical head may be configured to interfere with the pair of threads disposed on the inner surface of the screw hole to lock the screw into the screw hole once the screw is screwed into the screw hole.

In particular embodiments, each thread of the double helix threads of the screw may include a thread root, and the thread height of a portion of each thread disposed on the head may be shallow enough to enable the portion of the root disposed on the head to contact the pair of threads disposed on the inner surface of the screw hole when the screw is screwed into the screw hole. Depending upon design, a pitch of each thread on the head of the screw may be different than the pitch of the same thread on the body of the screw.

Depending upon design, the inner surface of the plate may further include a lower countersink, and the threaded portion may be disposed between the upper countersink and the lower countersink.

In particular embodiments, the threaded screw hole may be surrounded by a rim. Furthermore, the upper countersink may include a non-locking portion having a first countersink angle and a locking portion having a second countersink angle, and the non-locking portion may be disposed between the rim and the locking portion.

In particular embodiments, each thread of the pair of threads on the plate may have an included angle, and the second countersink angle may be equal to the included angle of each thread of the pair of threads.

Depending upon design, the screw may include a first material and the plate include a second material and the first material may be harder than the second material.

In particular embodiments, a method of using a screw and a locking fixation plate may include inserting a screw into a bone through a locking fixation plate. The locking fixation plate includes a threaded screw hole defined by an inner surface surrounding the threaded screw hole and the inner surface including an upper countersink and a threaded portion. Furthermore, the threaded portion may include a pair of threads arranged in a double helix configuration. The screw may include a generally conical head tapering into a generally cylindrical shaft that ends at a tip and a pair of threads beginning near the tip and extending along the generally cylindrical shaft and onto the generally conical head. Furthermore, a thread height on the screw may be constant over a majority of the generally cylindrical shaft and taper as the thread extends onto the head.

In particular embodiments, the method may further include rotating the screw in the screw hole such that the portion of the threads disposed on the generally conical head of the screw interfere with the helical pair of threads disposed on the inner surface of the screw hole to lock the screw into the screw hole.

In particular embodiments, the method may further include locking the screw into the screw hole at an angle other than parallel to a central axis of the screw hole.

Technical advantages of particular embodiments of the present disclosure include a double lead thread formed on the inside of the screw holes in the locking fixation plate that, as compared to a single lead thread, may enable a locking screw to engage the plate in half as many turns and engage the plate at an angle other than parallel to the central axis of the screw hole. Furthermore, each screw hole may include upper and lower countersinks that facilitate angled insertion of the bone screw through the plate by preventing the threading inside the screw hole from dictating the angle of insertion, and by providing clearance for the screw to tilt within the screw hole, yet another technical advantage. Also, the upper countersink may include both a locking portion and a non-locking portion. This feature may enable the threaded screw hole to accommodate either a locking screw or a non-locking screw, yet another technical advantage. Another technical advantage of the present invention relates to the double helix screw. Such a design permits the engagement of the screw within the plate and half as many turns. This feature, combined with the double-threaded feature of the fixation plate, accelerates the engagement and minimizes the amount of time the surgeon needs to install the fixation plates with the screws. Other technical advantages of the present disclosure will be readily apparent to one skilled in the art from the following figures, descriptions, and claims. Moreover, while specific advantages have been enumerated above, various embodiments may include all, some, or none of the enumerated advantages.

DETAILED DESCRIPTION OF THE INVENTION

For a more complete understanding of the present disclosure and its advantages, reference is now made to the following descriptions, taken in conjunction with the accompanying drawings, in which.

DETAILED DESCRIPTION

Figure 1:
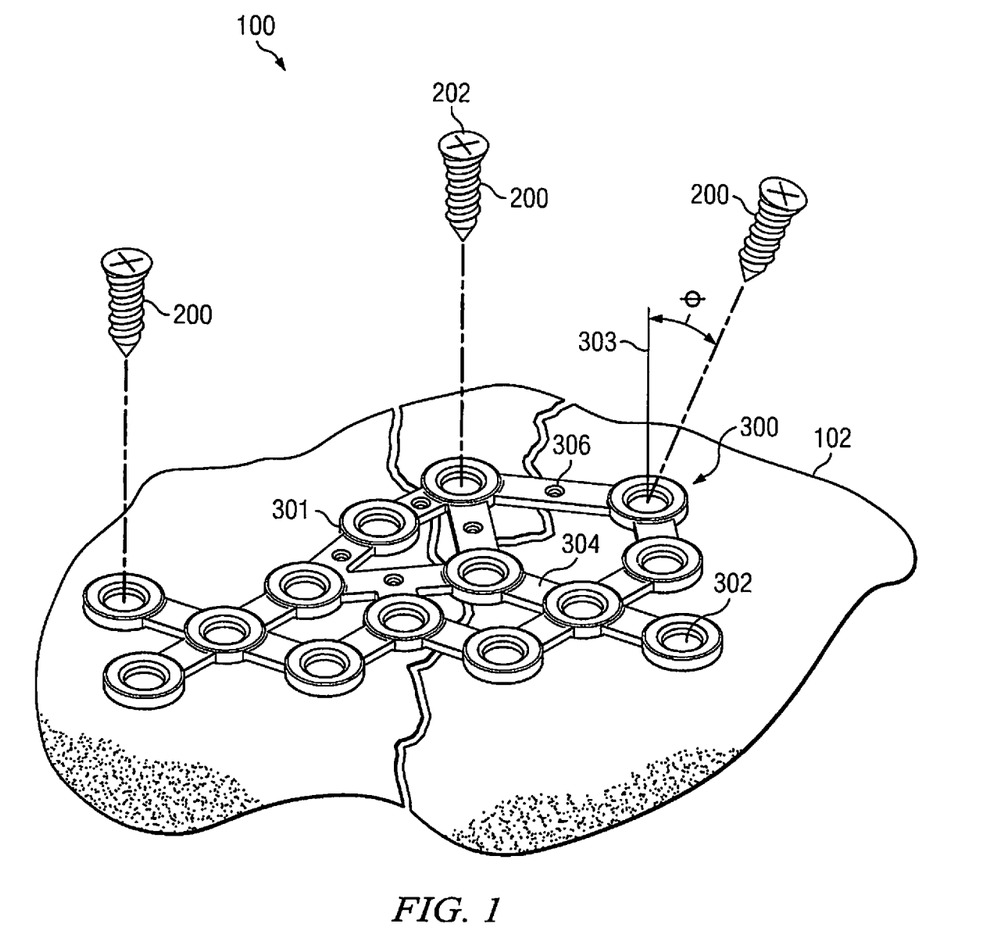
FIG. 1 illustrates an example embodiment of a system for attaching bone segments together including a locking plate and a plurality of locking screws according to the present disclosure.

FIG. 1 illustrates an example system 100 for attaching together bone segments according to an example embodiment of the present disclosure. In the pictured embodiment, system 100 is being used relative to a single fractured bone 102. However, particular embodiments of system 100 may be applied equally as well to virtually any bone or group of bones in the body. For example, system 100 may be used to attach bone 102 and another bone, or bone 102 and a synthetic element such as a surgical implant.

In particular embodiments, system 100 may include one or more locking screws 200 that may be used to secure a fixation plate 300 to bone 102. For reference purposes, fixation plate 300 and other components of system 100 may be referred to as having a top or upper or side intended to face away from bone 102 and a lower or bottom side intended to face toward bone 102 (e.g., to be placed upon bone 102). Though particular features of those components may be explained using such intended placement as a point of reference, this method of explanation is not meant to limit the scope of the present disclosure to any particular configuration of fixation plate 300, its features, or any other components, or to any particular placement or orientation of fixation plate 300 relative to bone 102.

Fixation plate 300 may generally include a body 301 comprising a plurality of threaded screw holes 302 connected to each other in a web-like distribution by a plurality of ribs 304, although any suitable geometry of plate 301 is contemplated. In particular embodiments, ribs 304 may be thinned down relative to threaded screw holes 302 to facilitate bending of ribs 304 rather than threaded screw holes 302 when fixation plate 300 is contoured, for example to match the contour of bone 102.

Depending upon design, one or more ribs 304 may comprise one or more positioning holes 306 that may be used to position fixation plate 300 relative to bone 102. As an example, to position fixation plate 300 relative to bone 102 using a positioning hole 306, a surgeon may insert one end of a Kirschner wire ("K-wire") into bone 102 near the desired location for fixation plate 300. The surgeon may then insert the free end of the K-wire through one of positioning holes 306 and slide fixation plate 300 down onto bone 102 using the K-wire as a guide. Additionally, the surgeon may rotate fixation plate 300 about the K-wire to achieve a desired orientation of fixation plate 300 relative to bone 102. Once fixation plate 300 has been properly positioned on bone 102, the surgeon may secure fixation plate 300 to bone 102 using, for example, one or more locking screws 200. The surgeon may then remove the K-wire from bone 102.

To secure fixation plate 300 to bone 102 using a locking screw 200, the surgeon may insert locking screw 200 through one of threaded screw holes 302 and into bone 102. Locking screw 200 may be inserted either parallel to the central axis 303 of screw hole 302, or at an angle θ relative to central axis 303. In certain procedures, the surgeon may pre-drill a pilot hole in bone 102 to establish the trajectory for locking screw 200, or, depending on design, locking screw 200 may be self-drilling in nature, making the pre-drilled hole in bone 102 unnecessary. In either case, once the tip 206 of locking screw 200 is contact with bone 102, the surgeon may use a screw driver or other suitable instrument to screw locking screw 200 into bone 102 until the head 202 of locking screw 200 comes to bear on the inner surface of screw hole 302. In particular embodiments, both the underside of head 202 and the inside of screw hole 302 may be threaded to permit locking screw 200 to lockably engage screw hole 302. In that case, further rotation of locking screw 200 at this point may cause the threaded portion of head 202 to interfere with the threading inside screw hole 302 and lock screw 200 into screw hole 302. The above-described process may be repeated for any suitable number of locking screw until locking plate 300 is firmly attached to bone 102. Once bone plate 300 has been secured to bone 102, the incision above bone 102 may be closed, leaving the patient to heal.

One of ordinary skill in the art will appreciate that the above-described embodiment and use of system 100 was presented for the sake of explanatory simplicity and will further appreciate that the present disclosure contemplates using any suitable number of locking screws 200 in combination with any suitable configuration of bone plate 300 to repair bone 102.

Figure 2A:
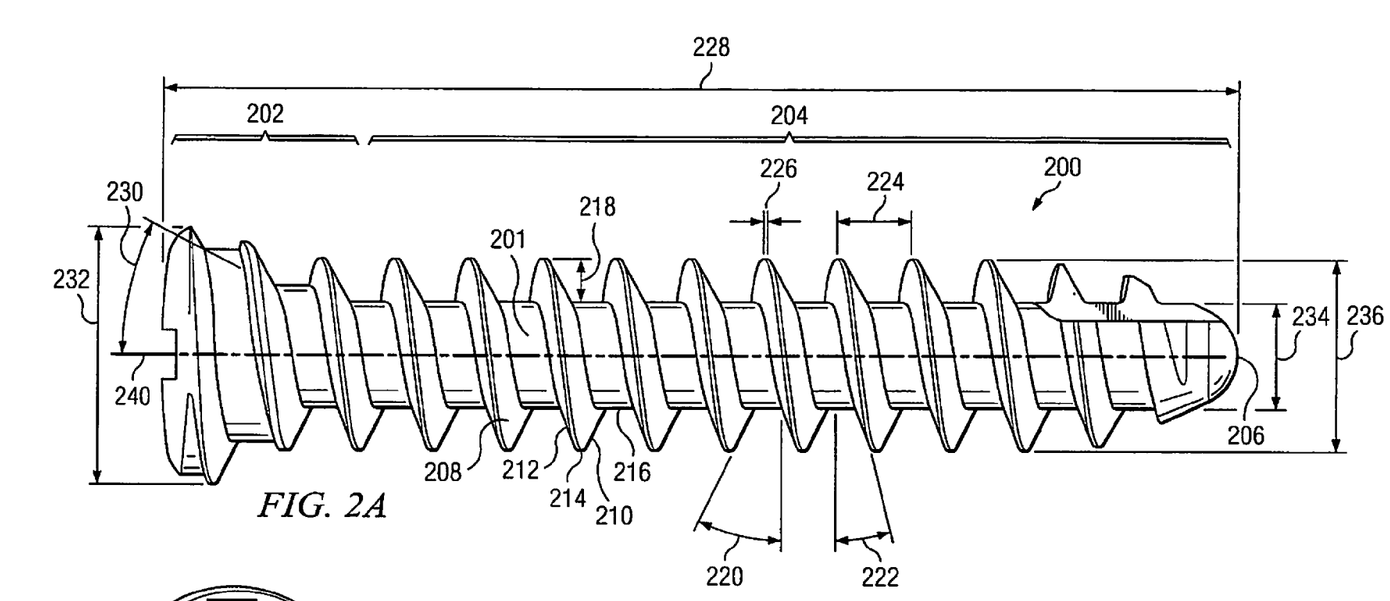
FIGS. 2A and 2B illustrate enlarged views of one of the locking screws of FIG. 1.
Figure 2B:
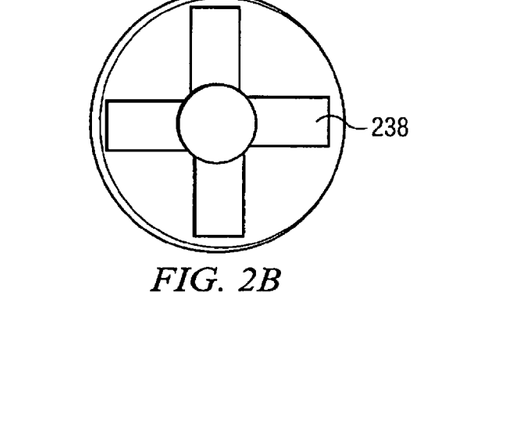

FIGS. 2A and 2B illustrate a more detailed view of one of the locking screws 200 of FIG. 1. In particular, FIG. 2A illustrates a side view of locking screw 200 taken perpendicular to the length of shaft 204, and FIG. 2B illustrates a top view of locking screw 200, looking down at the top side of head 202.

As illustrated in FIG. 2A, locking screw 200 generally includes a body 201 having a generally conical head 202 that tapers into a generally cylindrical shaft 204 ending at a tip 206. Screw 200 may further include a single generally continuous thread 208 formed around body 201 extending over a majority of locking screw 200 from tip 206 along the length of shaft 204 and onto head 202. In particular embodiments, screw 200 maybe formed by carving thread 208 out of a blank. This may enable head 202 to be low profile so as to minimize the profile thickness of the plate/screw interface when screw 200 is engaged with fixation plate 300.

Thread 208 may generally be defined by a leading flank 210, a trailing flank 212, a crest 214 connecting the outer edge of leading flank 210 to the outer edge of trailing flank 212, and a root 216 connecting the inner edge of leading flank 210 to the inner edge of trailing flank 212. The dimensions of thread 208 may generally be described by one or more of a thread height 218, a leading flank thread angle 220, a trailing flank thread angle 222, a pitch 224, a crest width 226, and a thread diameter 236. The dimensions of body 201 may generally be described by one or more of a length 228, a head taper angle 230, a head diameter 232, and a shaft diameter 234. Although screw 200 may be configured to any suitable size or shape, in particular embodiments, length 228 may range, for example, from 18 millimeters to 55 millimeters, thread height 218 may be about 0.030 in. along the length of shaft 204 and may decrease from 0.030 in to about 0.000 in. according to taper angle 230 over the length of head 202, taper angle 230 may be about 26 degrees, leading thread flank angle 220 may be about 30 degrees, trailing thread flank angle 222 may be about 10 degrees, pitch 224 may be about 0.054 in. along the length of shaft 204 and about 0.048 in. along the length of head 202, crest width 226 may be about 0.001 in. to 0.004 in. flat (e.g., wide), thread diameter 236 may be about 0.138 in., head taper angle 130 may be about 26 degrees, head diameter 232 may be about 0.176 in., and shaft diameter 234 may be about 0.078 in.

In particular embodiments, different portions of thread 208 may be configured to perform different functions. For example, the thread height 218 of the portion of thread 208 disposed on shaft 204 may be relatively large to enable thread 208 to bite into bone 102 along the length of shaft 204 while the thread height 218 of the portion of thread 208 disposed on head 202 may be relatively small along the length of head 202 to enable thread 208 and root 216 to interact with the threading inside screw hole 302 to lock screw 200 into plate 300. Depending upon design of screw 200, the pitch 224 of the portion of thread 208 disposed on shaft 204 may be the same as or different from the pitch 224 of the portion of thread 208 disposed on shaft 204 in order to enable screw 200 to lockably engage the threading on the inside of screw hole 302. As an example, pitch 224 may be constant along the entire length of screw 200.

As mentioned above, thread height 218 may taper as thread 208 extends onto head 202. This tapering may ensure that root 216 is brought into contact with the crest of the threading inside screw hole 302 when the threaded portion of head 202 comes to bear on the inner surface of screw hole 302. In particular, thread height 218 may be shallow enough on head 202 to enable the threading inside screw hole 302 to interact with (e.g., deform against or bite into) root 216 as well as thread 208. This dual interaction may increase the contact surface area between head 202 and the inner surface of screw hole 302 and provide a stable point of connection between plate 300 and screw 200, for example, when screw 200 is screwed into screw hole 302 at an angle other than perpendicular to the surface of screw hole 302. The desired locking effect may be caused by the threading inside screw hole 302 digging into thread 208 and root 216. If thread height 218 was not tapered on head 202 to enable root 216 to interact with the threading on the inner surface of screw hole 302, the threading inside screw hole 302 might only dig into thread 208, providing for a relatively weak point of connection.

The deformation process described above may be aided by forming screw 200 and plate 300 out of two materials having unequal hardness. For example, screw 200 may be formed of a material that is relatively softer than plate 300 to enable the threading inside screw hole 302 to dig into thread 208 and root 216. Alternatively, screw 200 may be formed of a material that is relatively harder than plate 300, in which case, the threading inside screw hole 302 may deform against thread 208 and root 216. In any case, the desired locking effect may be caused by threadable interface between the threading on head 202 and the threading in screw hole 302.

Depending upon design, screw 200 and plate 300 may be formed from any one or more materials suitable for forming medical implants, such as materials that have high strength-to-weight ratios and that are inert to human body fluids. In certain embodiments, screw 200 or plate 300 may be formed from one or more titanium alloys, which provide several benefits. For example, titanium alloys are relatively lightweight, provide adequate strength for withstanding forces typically experienced by a medical implant, are inert to human body fluids, and are visible in radiographs of the implant region. In a particular embodiment, screw 200 may be formed from the titanium based alloy Ti6Al4V ELI (per ASTM F136), and plate 300 may be formed from grade 2 or grade 3 titanium (per ASTM F67). In certain other embodiments, screw 200 or plate 300 may be formed from one or more resorbable polymers, such as polylactides, polyglycolide, glycolide/lactide copolymers or other copolymers, or one or more implantable plastics, such as polyethylene or acetal copolymers for example.

Since the desired locking effect described above between plate 300 and screw 200 may depend primarily upon the interface between the threading inside screw hole 302 and the threading on head 202, head 202 may lockably engage screw hole 302 independent of the size of shaft 204. Thus, shaft 204 may have virtually any configuration (e.g., fully threaded, partially threaded, self-threaded, unthreaded, long, or short) while still maintaining the ability to lockably engage plate 300 by virtue of its connection to head 202.

As shown in FIG. 2B, an engagement 238 is formed in head 202. In particular embodiments, engagement 238 may be adapted to receive an implantation tool such as a driver that may be used to rotate screw 200 about a longitudinal axis 240 in order to screw locking screw 200 into bone 102 and to lock locking screw 200 into screw hole 302. As an example, engagement 238 may comprises a cruciform-shaped recess adapted to mate with the screw driver; however, in other embodiments, engagement 238 may comprise any other suitable type of recess or engagement adapted to receive or mate with any suitable driver tool. For example, engagement 238 may comprise a recess having a hexagonal, rectangular, octagonal, or other shape. One of ordinary skill in the art will appreciate that the above described embodiments of locking screw 200 were presented for the sake of explanatory simplicity and will further appreciate that the present disclosure contemplates locking screw 200 having any suitable dimensions and configuration, being formed from any suitable materials, and being used for any suitable purpose.

Figure 3A:
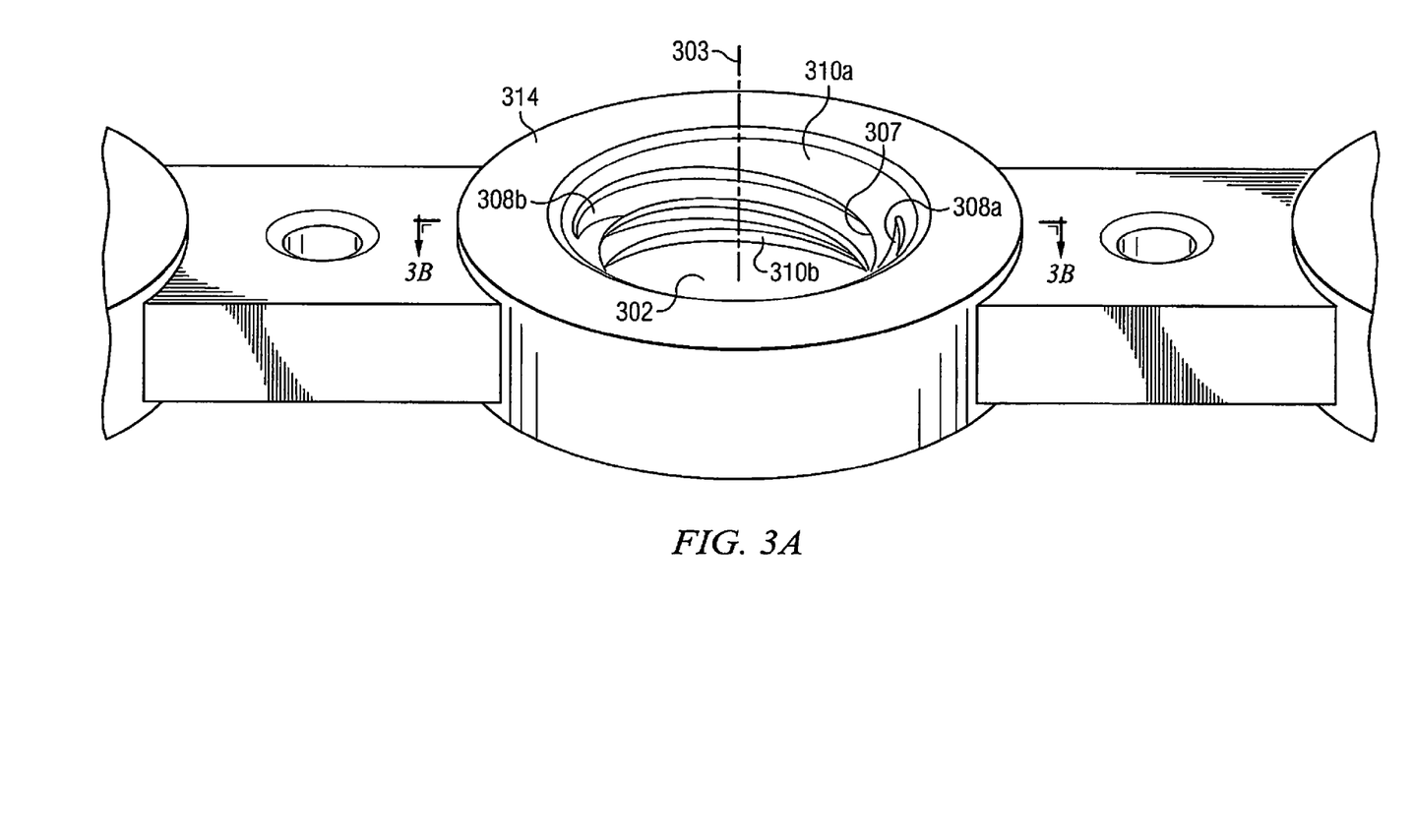
FIGS. 3A and 3B illustrate enlarged views of a locking screw hole that may be included in the locking plate of FIG. 1 according to the present disclosure.
Figure 3B:
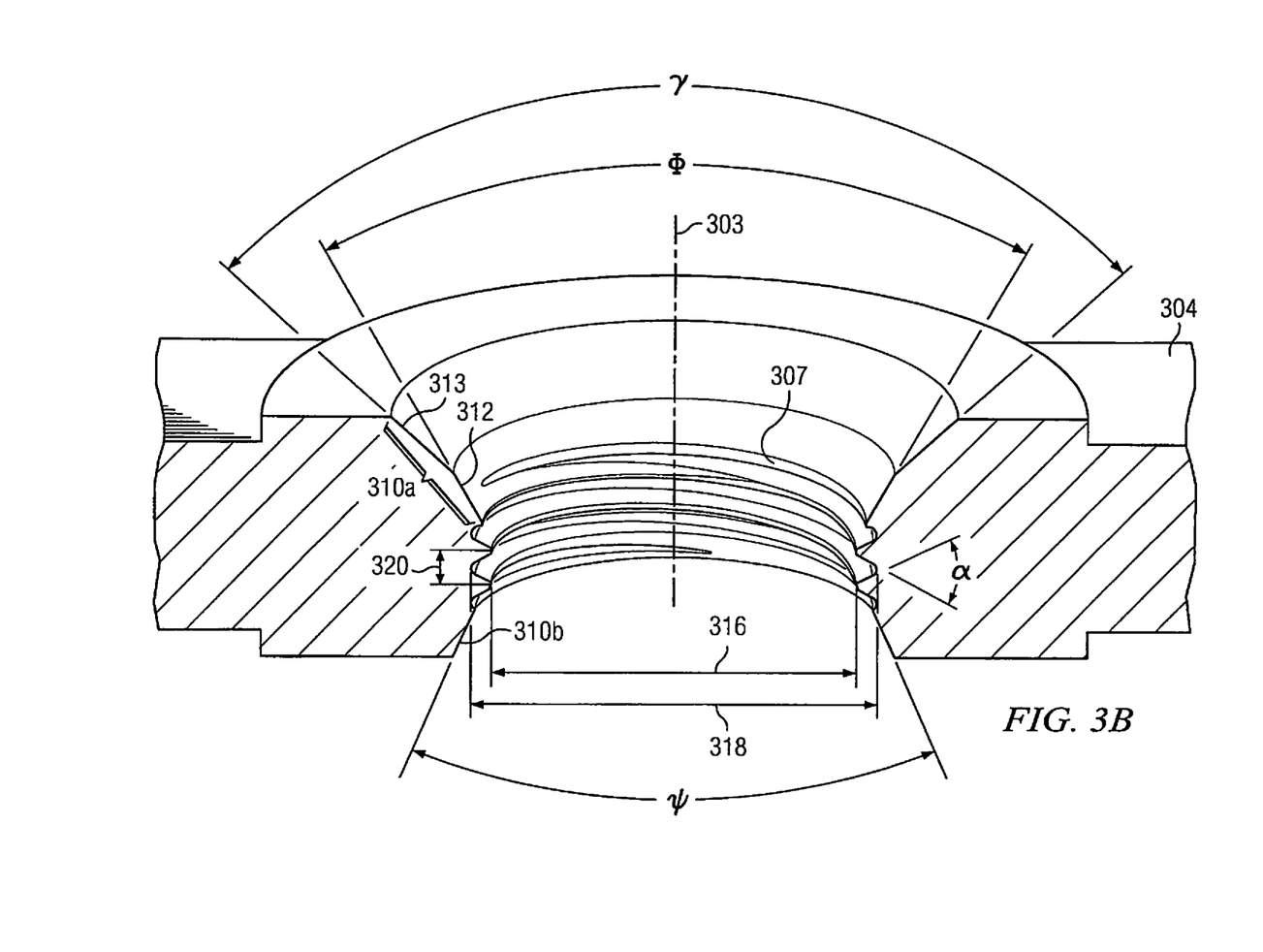

FIGS. 3A and 3B illustrate enlarged views of an example embodiment of a threaded screw hole 302 that may be included in locking plate 300 in accordance with the present disclosure. In particular, FIG. 3A depicts an isometric view of threaded screw hole 302 and FIG. 3B depicts a cross-sectional view of threaded screw hole 302 taken along line A of FIG. 3A.

Referring to FIG. 3A, threaded screw hole 302 may generally be defined by one or more of an upper countersink 310a, lower countersink 310b, and threaded portion 307 disposed between countersinks 310. Threaded screw hole 302 may further be surrounded by a rum 314 that comprises generally flat surface encircling threaded screw hole 302.

Depending upon design, threaded portion 307 may include double lead threads 308 comprising a first thread 308a arranged with a second thread 308b in a double helix configuration. As an example and not by way of limitation, threads 308a and 308b may be identical to one another in all respects (e.g., size, length, and included thread angle α), except that thread 308a may be opposed from thread 308b by 180 degrees. As compared to a single lead thread, double lead threads 308 may enable screw 200 to lockably engage plate 300 in half as many rotations, enable screw 200 to engage screw hole 302 at an angle other than parallel to the central axis 303 of threaded screw hole 302, and provide a greater amount of surface area to engage the threading on head 202, thereby increasing the force needed to disengage screw 200 from locking fixation plate 300.

Referring to FIG. 3B, in particular embodiments, upper counter sink 310a may include two portions, a locking portion 312 configured to lockably engage locking screw 200, and a non-locking portion 313 configured to seat a traditional screw having a non-locking (e.g., unthreaded) head. Locking portion 312 may be distinguished from non-locking portion 313 by the fact that threads 308 do not extend into non-locking portion 313. Including non-locking portion 313 on top of locking portion 312 may enable threaded screw hole 302 to accommodate either locking screw 200 or a traditional non-locking screw having a smooth under surface configured to bear against non-locking portion 313 when screwed into abode 102.

Depending upon design, locking portion 312 may be defined by a locking countersink angle Φ while, non-locking portion may 313 may be defined by a non-locking countersink angle γ. Lower counter sink 310b may also be defined by a lower countersink angle Ψ. Though countersinks 310 may have any suitable configuration, in particular embodiments, locking countersink angle Φ may be about 60 degrees, non-locking countersink angle γ may be about 90 degrees, and lower countersink angle Ψ may be about 60 degrees. In particular embodiments, the included angle α of threads 308a and 308b may be equal to locking countersink angle Φ.

Countersinks 310 may facilitate the ability of screw 200 to be inserted through screw hole 302 at an angle other than co-axial with central axis 303. For example, lower countersink 310b may provide clearance on the underside of plate 300 which enables shaft 204 to tilt within screw hole 302 up to a predefined angle before thread 208 (e.g., the threading on shaft 204) contacts the bottom surface of plate 300. Upper countersink 310a may enable screw 200 to lock into screw hole 302 at an angle other than perpendicular to the surface of screw hole 302 by preventing the threaded portion 307 from dictating the angle of insertion. When locking screw 200 is engaged with threaded screw hole 302, the portion of head 202 that is not engaged with threaded portion 307 may bear against upper countersink 310a to provide additional support for screw 200. In particular embodiments, upper countersink 310a may be deep enough to take in the entirety of head 202, even when head 202 is screwed into screw hole 302 at an angle other than parallel to the central axis 303 of threaded screw hole 302.

Referring back to threaded portion 307, threaded portion 307 may further be defined by one or more of a minor diameter 316, a major diameter 318, and a thread pitch 320. Although threaded portion 307 may be configured to any suitable size or shape, in particular embodiments, threaded portion 307 may include a double lead thread having a minor diameter 316 of 0.161+/−0.001 in., a major diameter 318 of 0.192+/−0.001 in. and a thread pitch 320 of 0.028 in.

Furthermore, in particular embodiments, the outer edges of head 202 may be beveled to enable the edges of head 202 to remain below the plane of rim 314, even when inserted into screw hole 302 at an angle. Thus, the low profile of head 202 in combination with the custom size of countersinks 310 may provide a low plate/screw profile and reduce patient palpation of the implant (e.g., plate 300 and screw 200) by enabling head 202 to sink below the plane of rim 314 while still maintaining the desired angular locking interface.

Figures 4A, 4B, 4C:
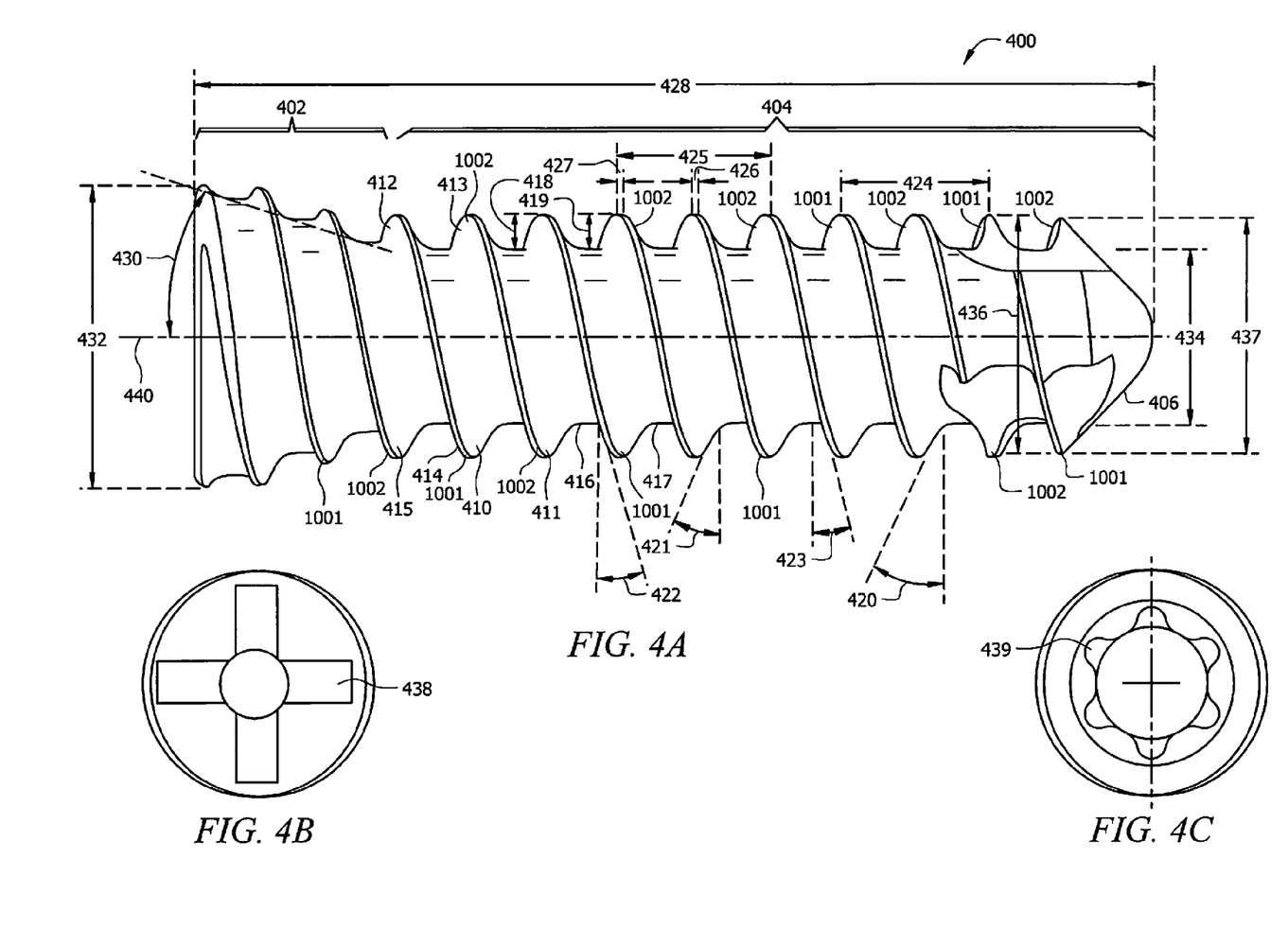
FIGS. 4A, 4B and 4C illustrate enlarge views of double helix locking screws.

FIGS. 4A and 4B illustrate a more detailed view of the double helix locking screws 400. In particular, FIG. 4A illustrates a side view of locking screw 400 taken perpendicular to the length of shaft 404, and FIG. 4B illustrates a top view of locking screw 400, looking down at the top side of head 402.

Figure 5:
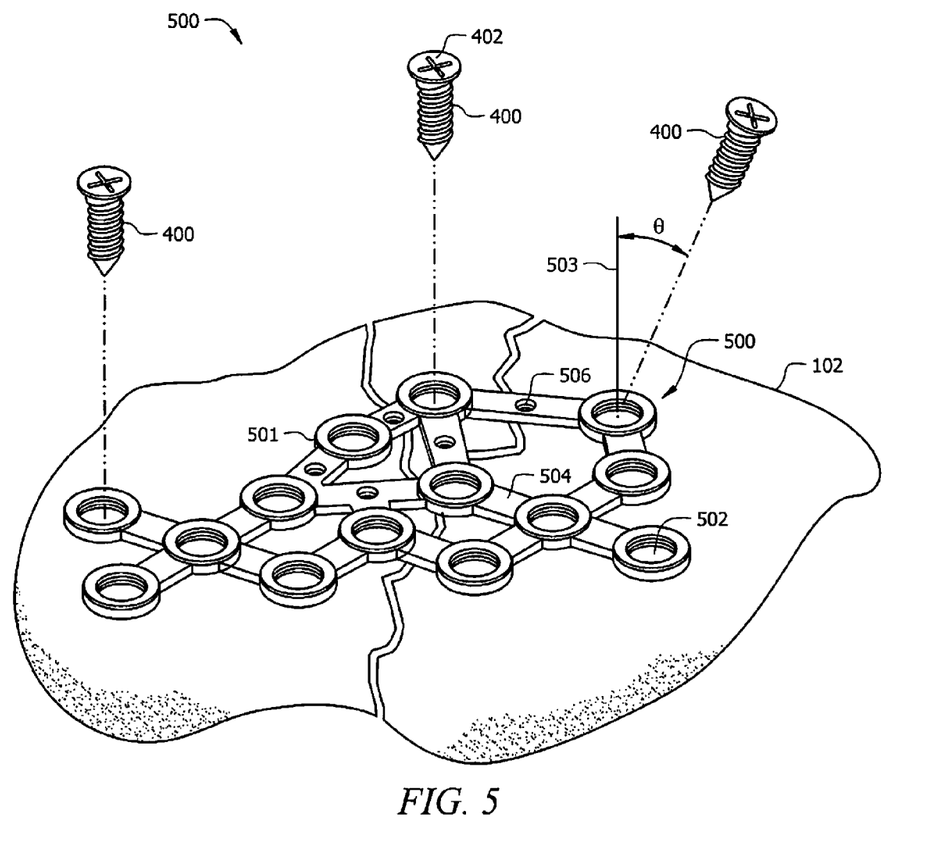
FIG. 5 illustrates an example embodiment of a system for attaching bone segments together, including a locking plate and a plurality of double helix locking screws according to the present disclosure.

As illustrated in FIG. 4A, locking screw 400 generally includes a body 401 and a generally conical head 402 that tapers into a generally cylindrical shaft 404 ending at a tip 406. Screw 400 further includes two generally continuous threads 1001 and 1002 intertwined in a double helix format. Threads 1001 and 1002 extend over the majority of locking screw 400 from tip 406 along the length of shaft 404 onto head 402. In particular embodiments, screw 400 may be formed by carving threads 1001 and 1002 out of a blank. This may enable head 402 to be low-profile so as to minimize the profile thickness of the plate/screw interface when screw 400 is engaged within a fixation plate 500, as shown in FIG. 5.

Figure 4D:
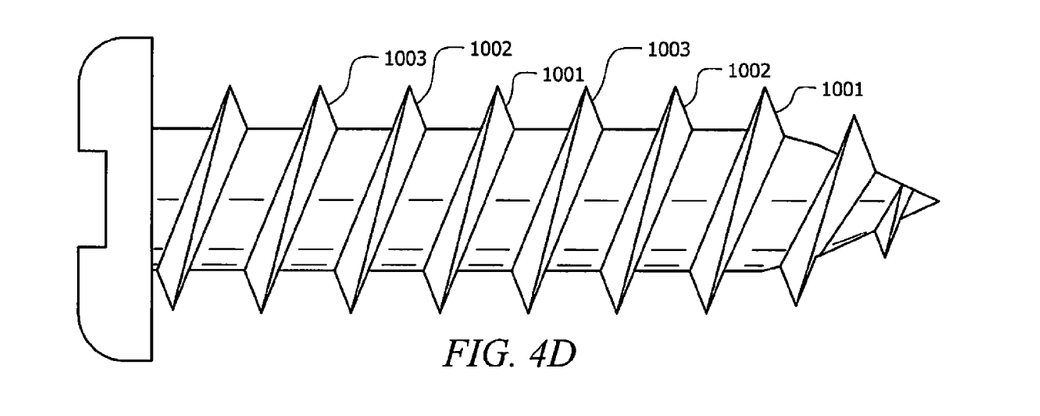
FIGS. 4D and 4E illustrate multihelix locking screws.
Figure 4E:
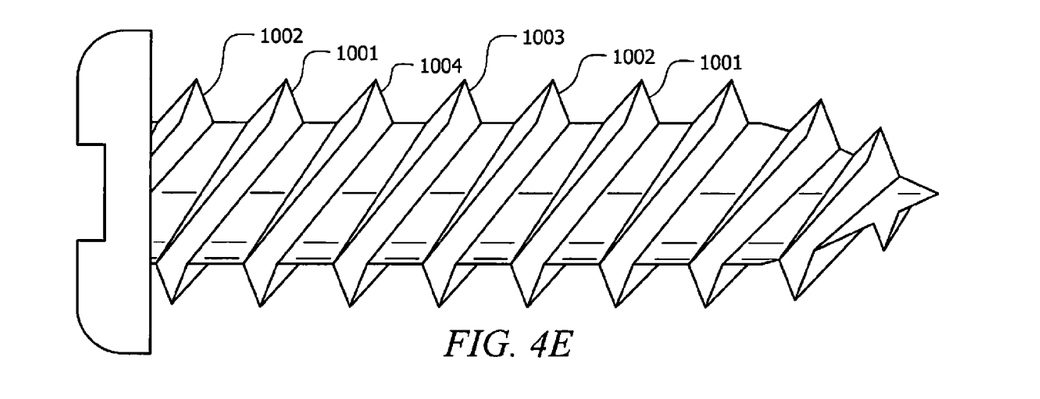

Each double helix thread 1001 and 1002 may generally be defined by a leading flank 410/411, a trailing flank 412/413, and a crest 414/415 connecting the outer edge of respective leading flank 410/411 to the corresponding outer edge of trailing flank 412/413. Each thread includes a root 416/417. It will be understood by one skilled in the art that since threads 1001 and 1002 are overlapping and helical in nature, the descriptions previously provided with respect to the characteristics of a single thread, as discussed above in FIGS. 2A and 2B, apply in a similar manner with respect to FIGS. 4A and 4B, except that there are two threads interspaced and helical in characteristics. The use of a helical threads accelerates the advancement of the screw into the anchoring material due to the multiple use of threads. It will be understood by one skilled in the art that the use of a double helix screw 400 may include more than two interspaced threads, such as three or four interspaced threads, as shown in FIGS. 5, 4D and 4E as multiple threads 1001/1002/1003 in the case of FIG. 4D and threads 1001/1003/1003/1004 in the case of FIG. 4E. Such designs will advance the screw quicker due to the triple or quadruple nature of the screw threads. It will be understood by one skilled in the art that the disclosure herein is intended to cover the use of triple, quadruple or multiple threaded screws and is not limited to a double helix screw.

As discussed in FIG. 2A above, the dimensions of threads 1001 and 1002 in FIG. 4 may generally be described by one or more of a corresponding thread height 418/419. Similarly, the dimensions of thread 1001 and 1002 may be described by a corresponding leading flank thread angle 420/421, a corresponding trailing flank thread angle 422/423, a corresponding pitch 424/425, a corresponding crest width 426/427, and thread diameter 436. Additionally, the thread diameters of each thread 1001/1002 may vary, which provides additional engagement and threading characteristics.

The dimensions of body 401 may generally be described by one or more of a length 428, a head angle 430, a head diameter 432, and a shaft diameter 434. Although screw 400 may be configured to any suitable size or shape, in particular embodiments, length 428 may range, for example, from 10 mm to 70 mm, thread height 418/419 may be about 0.030 inches along the length of shaft 404, and may decrease from 0.030 inches to about 0.000 inches according to the taper of angle 430 over the length of head 402. Head angle 430 defines the general tapered angle of the conical head 402 and may be between about 15 and 20 degrees and preferably about 18 degrees. Leading thread flank angle 420/421 may be about 30 degrees. Trailing flank angle 422/423 may be about 10 degrees. Pitch 424/425 may be about 0.049 inches along the length of shaft 404 and about 0.044 inches along the length of head 402. Crest width 426/427 may be about 0.001 inches to about 0.004 inches flat (e.g., wide). Thread diameter 436 may be about 0.138 inches and thread diameter 437 may be about 0.138 inches. Diameter 432 may be about 0.196 inches, and shaft diameter 434 may be about 0.094 inches. Referring still to FIG. 4A, crests 426/427 gradually terminate into the end of the conical portion 402, distal from the tip 406. This provides for a smooth transition and across the conical portion 402 and a flat top when seated within screw hole 502 as discussed further below.

In particular embodiments, different portions of thread 1001/1002 may be configured to perform different functions. For example, to enable thread 1001/1002 to bite into bone 102, the thread height 418 and/or 419 may vary along the length of shaft 404 along the length of head 402 to interact with the double helix threading inside screw hole 502 (FIG. 5) to lock screw 400 into plate 500. Depending upon the design of screw 400, the corresponding pitch 424 of thread 1001 or pitch 425 of thread 1002 may be the same as, or different from, the pitch of the threads located within fixation plate 500.

FIG. 5 illustrates a system 500, which is identical to system 100, as noted above, other than its preparation for inclusion of screws 400, rather than 200. That is, system 500 is intended to be employed with the double helix screws 400. The description of system 500, and in particular fixation plate 500 is identical to fixation plate 300, as noted in FIG. 1. Its configuration is similar to that, as shown in FIG. 1, comprising fixation plate 300. Fixation plate 500 may generally include a body 501 comprising a plurality of threaded screw holes 502 connected to each other in a web-like distribution by a plurality of ribs 504, although any suitable geometry of plate 501 is contemplated. In particular embodiments, ribs 504 may be thinned down relative to threaded screw holes 502 to facilitate bending of ribs 504 rather than threaded screw holes 502 when fixation plate 300 is contoured, for example to match the contour of bone 102. Its implementation would be identical to that with respect to fixation plate 300. That is, securing fixation plate 500 to bone 102 uses the locking screw 400, as discussed above. As in the case of plate 300, the surgeon may insert locking screw 400 through one or more threads screw holes 502 and into bone 102. Locking screw 400 may be inserted either parallel to the central axis 503 of screw hole 502, or at an angle θ relative to central angle 503. In certain procedures, the surgeon may pre-drill a pilot hole in bone 102 to establish a trajectory for locking screw 400, or, depending on design, locking screw 400 may be self-drilling in nature, making the pre-drilled hole in bone 102 unnecessary. In either case, once the tip 406 of locking screw 400 is in contact with bone 102, the surgeon may use a screwdriver or other suitable instrument to screw locking screw 400 into bone 102 until the head 402 of locking screw 200 come to bear against the end of the surface of screw hole 502. In particular embodiments, both the underside of head 402 and the inside of screw hole 502 may be threaded to commit locking screw 400 to lockably engage screw hole 502. In that case, further rotation of locking screw 400 may cause the threaded portion of head 402 to interfere with the threading inside screw hole 502 and lock screw 400 into screw hole 502. The above-described process may be repeated for any suitable number of locking screws until plate 500 is firmly attached to bone 102. Once the fixation plate 500 has been secured to bone 102, the incision about 102 may be closed, leaving the patient to heal.

In this manner, the double helix threaded screw, as shown in FIG. 4A, may interact with the double helix thread shown within plate 500. In particular, thread height 418/419 may be shallow enough on head 402 to enable the threading inside screw hole 502 to interact with (e.g., deform against or bite into) the threads within hole 502. And, as noted above, since crests 426/427 gradually terminate into the end of the conical portion 402, distal from the tip 406, the top of conical portion 402 is flat with the top of screw hole 502. Further, the present invention provides that the configuration and design of the threads located within screw hole 502 would be identical to that shown and described above with respect to FIGS. 3A and 3B. In this manner, screw 400 is inserted within screw hole 502 which has the tapered and threaded configurations as noted above with respect to FIGS. 2A and 2B within FIGS. 3A and 3B except that a double helix screw is used as noted above and described in FIGS. 4A, 4B, and 4C. Thus, the dual interaction between head 402 and the inner surface of screw hole 502 provides a stable point of connection between plate 500 and screw 400. Such would occur once screw 400 is screwed into screw hole 502 at an angle other than perpendicular to the surface of screw hole 502. The desired locking effect may be caused by the threading inside screw hole 502 digging into threads 1001 and 1002 and their corresponding roots 416 and 417.

The deformation process described above may be aided by forming screw 400 into plate 500 out of two materials having unequal hardness. For example, screw 400 may be formed of a material that is relatively softer than plate 500 to enable the threading inside screw hole 502 to dig into threads 1001 and 1002 in corresponding root 416/417.

Alternatively, screw 400 may be formed of a material that is relatively harder than plate 500, in which case the threading inside screw hole 502 may deform against threads 1001 and 1002 in corresponding root 416/417. In any case, the desired locking effect may be caused by threadable interface between the threading of head 402 and the threading in screw hole 502.

Depending upon design, screw 400 and plate 500 may be formed from any one or more materials suitable for forming medical implants, such as materials that have high strength-to-weight ratios and that are inert to human body fluids. In certain embodiments, screw 400 or plate 500 may be formed from one or more titanium alloys, which provide several benefits. For example, titanium alloys are relatively lightweight, provide adequate strength for withstanding forces typically experienced by a medical implant, are inert to human body fluids, and are visible in radiographs of the implant region. In a particular embodiment, screw 400 may be formed from the titanium based alloy Ti6Al4V ELI (per ASTM F136), and plate 300 may be formed from grade 2 or grade 3 titanium (per ASTM F67). In certain other embodiments, screw 400 or plate 500 may be formed from one or more resorbable polymers, such as polylactides, polyglycolide, glycolide/lactide copolymers or other copolymers, or one or more implantable plastics, such as polyethylene or acetal copolymers for example.

Since the desired locking effect described above between plate 500 and screw 400 may depend primarily upon the interface between the threading inside screw hole 502 and the threading on head 402, head 402 may lockably engage screw hole 502 independent of the size of shaft 404. Thus, shaft 404 may have virtually any configuration (e.g., fully threaded, partially threaded, self-threaded, unthreaded, long, or short) while still maintaining the ability to lockably engage plate 500 by virtue of its connection to head 402.

As shown in FIG. 4B, an engagement 438 is formed in head 402. In particular embodiments, engagement 438 may be adapted to receive an implantation tool such as a driver that may be used to rotate screw 400 about a longitudinal axis 440 in order to screw locking screw 400 into bone 102 and to lock locking screw 400 into screw hole 502. As an example, engagement 438 may comprises a cruciform-shaped recess adapted to mate with the screw driver or, as shown in FIG. 4C, the engagement 439 may comprise a hexalobe or star-shaped recess. However, engagement 438/439 may comprise any other suitable type of recess or engagement adapted to receive or mate with any suitable driver tool. For example, engagement 438/439 may comprise a recess having a hexagonal, rectangular, octagonal, or other shape. One of ordinary skill in the art will appreciate that the above described embodiments of locking screw 400 were presented for the sake of explanatory simplicity and will further appreciate that the present disclosure contemplates locking screw 400 having any suitable dimensions and configuration, being formed from any suitable materials, and being used for any suitable purpose.

One of ordinary skill in the art will appreciate that the above-described embodiments were presented for the sake of explanatory simplicity and will further appreciate that the present disclosure contemplates any suitable configuration and number of screw holes 302, ribs 304, and positioning holes 306 in fixation plate 300; and screw holes 502, ribs 504, and positioning holes 506 in fixation plate 500. Moreover, although the present disclosure, including the fixation system and the screw, collectively and individually, has been described in several embodiments, a myriad of changes, substitutions and modifications may be suggested to one skilled in the art, and it is intended that the present disclosure encompasses such changes, substitutions and modifications as fall within the scope of the present appended claims.

What is claimed is:

1. A system for lockably engaging bone screws into a fixation plate, comprising:
a locking fixation plate including a threaded screw hole defined by an inner surface surrounding the threaded screw hole, the inner surface comprising an upper countersink and a threaded portion, the threaded portion comprising a pair of threads arranged in a double helix configuration, wherein an end of a first thread of the pair of threads, proximate the upper countersink, is approximately 180° from an end of a second thread of the pair of threads; and
a screw comprising a generally conical head tapering into a generally cylindrical shaft that ends at a tip and at least two threads arranged in a helix configuration beginning near the tip and extending along the generally cylindrical shaft and onto the generally conical head, a thread height of each thread being generally constant over a majority of the generally cylindrical shaft and tapering as the thread extends onto the head,
wherein the portion of the threads disposed on the generally conical head is configured to interfere with the pair of threads disposed on the inner surface of the screw hole once the screw is screwed into the screw hole to lock the screw into the screw hole.

2. The system of claim 1, wherein:
the screw comprises three threads arranged in a helix configuration.

3. The system of claim 1, wherein:
the screw comprises four threads arranged in a helix configuration.

4. The system of claim 1, wherein:
each thread of the screw comprises a thread root; and
the thread height of a portion of each thread disposed on the head is shallow enough to enable the portion of the root of that same thread disposed on the head to contact the pair of threads disposed on the inner surface of the screw hole when the screw is screwed into the screw hole.

5. The system of claim 1, wherein a pitch of a thread on the head of the screw is different than a pitch of that same thread on the body of the screw.

6. The system of claim 1, wherein:
the inner surface further comprises a lower countersink; and
the threaded portion is disposed between the upper countersink and the lower countersink.

7. The system of claim 1, wherein:
the threaded screw hole is surrounded by a rim;
the upper countersink comprises a non-locking portion having a first countersink angle and a locking portion having a second countersink angle; and
the non-locking portion is disposed between the rim and the locking portion.

8. The system of claim 7, wherein the first countersink angle is different from the second countersink angle.

9. The system of claim 7, wherein each thread of the pair of threads comprises an included angle; and
the second countersink angle is equal to the included angle of each thread of the pair of threads.

10. The system of claim 1, wherein the screw comprises a first material and the plate comprises a second material; and
the first material is harder than the second material.

11. A system for lockably engaging bone screws into a fixation plate, comprising:
a locking fixation plate including a threaded screw hole defined by an inner surface surrounding the threaded screw hole, the inner surface comprising an upper countersink and a threaded portion, the threaded portion comprising a pair of threads arranged in a double helix configuration, wherein at least a portion of the double helix configuration is cylindrical; and
a screw comprising a generally conical head tapering into a generally cylindrical shaft that ends at a tip and at least two thread arranged in a helix configuration beginning near the tip and extending along the generally cylindrical shaft and onto the generally conical head, a height of each thread being generally constant over a majority of the generally cylindrical shaft and tapering as each such thread extends onto the head,
wherein the portion of the threads disposed on the generally conical head is configured to interfere with the pair of threads disposed on the inner surface of the screw hole once the screw is screwed into the screw hole to lock the screw into the screw hole.

12. The system of claim 11, wherein:
the screw comprises three threads arranged in a helix configuration.

13. The system of claim 11, wherein:
the screw comprises four threads arranged in a helix configuration.

14. The system of claim 11, wherein:
each thread of the screw comprises a thread root and the thread height of a portion of each thread disposed on the head is shallow enough to enable the portion of the root of that same thread disposed on the head to contact the pair of threads disposed on the inner surface of the screw hole when the screw is screwed into the screw hole.

15. A system for lockably engaging bone screws into a fixation plate, comprising:
- a locking fixation plate including a threaded screw hole defined by an inner surface surrounding the threaded screw hole, the inner surface comprising an upper countersink and a threaded portion, the threaded portion comprising a pair of threads arranged in a double helix configuration, wherein at least a portion of the double helix configuration is cylindrical; and
- a screw comprising a generally conical head tapering into a generally cylindrical shaft that ends at a tip and at least two thread arranged in a helix configuration beginning near the tip and extending along the generally cylindrical shaft and onto the generally conical head, a height of each thread being generally constant over a majority of the generally cylindrical shaft and tapering as each such thread extends onto the head, wherein the portion of the threads disposed on the generally conical head is configured to interfere with the pair of threads disposed on the inner surface of the screw hole once the screw is screwed into the screw hole to lock the screw into the screw hole, wherein each thread of the screw comprises a thread root and the thread height of a portion of each thread disposed on the head is shallow enough to enable the portion of the root of that same thread disposed on the head to contact the pair of threads disposed on the inner surface of the screw hole when the screw is screwed into the screw hole.

16. The system of claim 15, wherein:
the screw comprises three threads arranged in a helix configuration.

17. The system of claim 15, wherein:
the screw comprises four threads arranged in a helix configuration.

* * * * *